(12) United States Patent
Stoelwinder et al.

(10) Patent No.: US 7,910,756 B2
(45) Date of Patent: Mar. 22, 2011

(54) PROCESS FOR THE PREPARATION 2-SUBSTITUTED-DERIVATIVES OF ESTRONE AND ESTRADIOL

(75) Inventors: Johannes Stoelwinder, Oss (NL); Nicolaas Elisabeth Cornelis Moers, Oss (NL)

(73) Assignee: N.V. Organon, Oss (NL)

( * ) Notice: Subject to any disclaimer, the term of this patent is extended or adjusted under 35 U.S.C. 154(b) by 877 days.

(21) Appl. No.: 11/659,147

(22) PCT Filed: Aug. 1, 2005

(86) PCT No.: PCT/EP2005/053732
§ 371 (c)(1),
(2), (4) Date: Feb. 1, 2007

(87) PCT Pub. No.: WO2006/013196
PCT Pub. Date: Feb. 9, 2006

(65) Prior Publication Data
US 2009/0012319 A1    Jan. 8, 2009

(30) Foreign Application Priority Data
Aug. 4, 2004 (EP) .................................. 04103742

(51) Int. Cl.
*C07J 1/00* (2006.01)
(52) U.S. Cl. .................. 552/614; 552/626; 552/627
(58) Field of Classification Search .......... 549/614, 549/626, 627; 552/614, 626, 627
See application file for complete search history.

(56) References Cited

U.S. PATENT DOCUMENTS

| | | |
|---|---|---|
| 3,186,907 A | 6/1965 | Nomine et al. |
| 3,519,714 A | 7/1970 | Hughes et al. |
| 4,400,524 A | 8/1983 | Huber |
| 5,504,074 A | 4/1996 | D'Amato et al. |
| 5,521,168 A | 5/1996 | Clark |
| 5,661,143 A | 8/1997 | D'Amato et al. |
| 5,892,069 A | 4/1999 | D'Amato et al. |
| 5,998,639 A | 12/1999 | Raijmakers et al. |
| 6,051,726 A | 4/2000 | Sachdeva et al. |
| 7,087,592 B1 | 8/2006 | Agoston et al. |
| 7,235,540 B2 | 6/2007 | Agoston et al. |
| 2004/0097479 A1 | 5/2004 | Agoston et al. |
| 2006/0025619 A1 | 2/2006 | Agoston et al. |

FOREIGN PATENT DOCUMENTS

| | | |
|---|---|---|
| BE | 616293 | 10/1962 |
| DE | 3208432 | 9/1983 |
| EP | 0776904 | 3/2000 |
| GB | 2116165 | 9/1983 |
| WO | WO 01/14405 | 3/2001 |
| WO | WO 02/42319 | 5/2002 |

OTHER PUBLICATIONS

International Search Report and Written Opinion for PCT/EP2005/053732 dated Nov. 4, 2005.
Ali et al.,"Synthesis and Receptor Binding Affinity of 7α- and 17α-Substituted 2- and 4-Chlorpestragliel Derivatives," *J. Chem. Soc. Perkin Trans. 1* (1991) 2485-2491.
Axelrod et al., "Synthesis of 2-Hydroxyestradiol-17β," *Chem. & Ind.* (1959) 1454-1455.
Antonaccio, L.D., et. al., Preparation and Nuclear Magnetic Resonance Spectra of 11-Oxygenated Estrogen Catechols, J. Org. Chem., 36 (1971) 1832-1835.
Banerjee et al., "2-Methoxyestradiol inhibits estrogen-induced pituitary tumor angiogenesis and suppresses tumor growth in Fisher 344 rats," *Proc. Amer. Assoc. Cancer Res. 39*, (1998) 385.
Fishman, "Synthesis of 2-Methoxyestrogens," *J. Am. Chem. Soc. 80* (1958) 1213-1215.
Le Quesne et al., "Novel Synthesis of 2-Fluoroestradiol from 19-Nortestosterone: Biomimetic Oxidative Defluorination to 2-Hydroxyestradiol," *Steroids 53/6* (1989) 649-661.
Mihailovic et al., "A Novel Procedure for the Aromatization of Ring A in 19-Nortestosterone," *Tetrahedron 33* (1977) 235-237.
Opposition against Patent Application No. PCT-07-7228 dated Feb. 5, 2007 in the name of N.V. Organon. Filed by Western Pharmaceutical S.A., Ecuador.

*Primary Examiner* — Bernard Dentz

(57) ABSTRACT

The invention provides a process for the preparation of 2-substituted-derivatives of estrone and estradiol. The invention also provides several novel compounds, which can be intermediates in the process, and processes to prepare these novel compounds. The invention also provides 2-alkoxy-estrone, 2-alkoxy-estradiol or mixtures thereof essentially free from other estrogenic intermediates.

5 Claims, 2 Drawing Sheets

PROCESS FOR THE PREPARATION 2-SUBSTITUTED-DERIVATIVES OF ESTRONE AND ESTRADIOL

TECHNICAL FIELD

This invention relates to a process for the preparation of 2-substituted-derivates of estrone and estradiol.

BACKGROUND OF THE INVENTION

The therapeutic value of 17-keto steroids or 17-hydroxy steroids such as estrone and estradiol are well known. In addition to the steroids itself, also derivatives of estrone and estradiol have been found to have therapeutic value. In this respect especially 2-alkoxy-derivates of estrone and estradiol, such as 2-methoxy-estradiol, need to be mentioned.

2-methoxyestradiol, 1,3,5(10)-estratrien-2,3,17b-triol-2-methyl-ether (2-ME2) is an endogenous metabolite of estradiol. 2-ME2 has low estrogenic activity, but has been found to have important other biological effects, such as anti-cancer activity, as described herein below.

U.S. Pat. Nos. 5,504,074, 5,66,143 and 5,892,069 describe methods of treating mammalian diseases characterized by abnormal cell mitosis using 2-ME2. In addition WO-A-02/42319 describes 2-ME2 for the treatment of disease states characterized by abnormal angiogenesis.

Undesirable cell mitosis is characteristic of many diseases, including, but not limited to, cancer, atherosclerosis, proliferation of solid tumors, vascular malfunctions, endometriosis, retinopathies, arthropathies, and abnormal wound healing. In addition, cell mitosis is important in a wide variety of biological functions, including but not limited to the normal development of the embryo, formation of the corpus luteum, cyclic proliferation of uterine endometrium, wound healing and inflammatory and immune responses.

U.S. Pat. No. 5,521,168 describes the use of 2-ME2 for lowering intraocular pressure. 2-ME2 also inhibits estrogen-induced pituitary tumor angiogenesis and suppresses tumor growth in Fisher 344 rats as reported by Banerjee, S. K. et al., Proc. Amer. Assoc. Cancer Res. 39, March 1998.

Any therapeutic use of 2-ME2 in humans requires 2-ME2 having a high level of purity. In particular, since 2-ME2 has effects that are counteracted by estradiol and other estrogenic metabolites, it is desirable to have a 2-ME2 preparation substantially free of such contaminants. Effects that may be seen from contaminating estradiol, estrone and 2-hydroxyestradiol include estrogenic effects such as feminization, endometrial proliferation, increased risk of uterine and breast cancer, developmental effects on sexual organs, inhibition of leucopoiesis and effects on haematopoietic cells. In addition, 4-hydroxyestradiol, 4-methoxyestradiol and estradiol are known to be at least suspected carcinogens.

These findings have prompted us to search for new synthetic procedures for the preparation of 2-alkoxy derivatives of estrone and estradiol such as 2-methoxyestradiol Processes for the preparation of 2-ME2 are known in the art. For example, the article titled "Synthesis of 2-methoxyestrogens" by J. Fishman, published in the J. Am. Chem. Soc., 5 Mar. 1958, pages 1213-1216, describes the preparation of 2-methoxy-estradiol starting from estradiol. Also U.S. Pat. No. 6,051,726 describes the preparation of 2-alkoxyestradiols starting from estradiol. A disadvantage of such processes starting from estradiol, however, is the risk that the final product 2-ME2, will be contaminated with undesired estrogenically active compounds, such as the starting compound estradiol and/or any estrogenic intermediates. As explained above, such estrogenic impurities are highly undesirable.

EP-A-0776904 relates to the completely different technical field of the preparation of alkylketals of 3-keto-5(10),9 (11)-gonadiene-derivatives. In its examples the preparation of such a gonadiene-derivative starting from estra-4,9-diene-3,17-dione is described. The estra-4,9-diene-3,17-dione compound is prepared by condensing (+)5α-hydroxy-7aβ-methyl-2,3,3aα,4,5,6,7,7a-octahydro-1H-inden-1-one-4α-(3-propionic acid)-lacton with 2-pentanone-neopentylacetale-5-magnesium chloride; oxidizing the 5α-hydroxy group; ring closure of the first ring (B); ketal cleavage; and ring closure of the second ring (A). EP-A-0776904 does not describe nor suggest the preparation of 2-substituted derivatives of estra-4,9-diene-3,17-dione.

Furthermore H. Ali et al, J. Chem. Soc. Perkin Trans. 1, 1991, page 2485-2491 describe the possibility of a route using 19-norsteroids with a suitable located double bond, followed by selective introduction of a functional group at position C2 or C4 and subsequent aromatization of the A-ring into 2- or 4-substituted-estradiol. No specific examples of such a 2-substitution according to this route were given.

Other preparations of 2-substituted estradiols are described in P. W. Le Quesne et al, Steroids, vol. 53/6, June 1989, page 649-661; L. R. Axelrod et al, Chem.&Ind., November 1959, page 1454-1455; and M. Mihailovic, Tetrahedron, vol. 33, 1977, page 235-237.

BRIEF DESCRIPTION OF THE DRAWINGS

The following figures have been enclosed to illustrate the present invention.

SUMMARY OF THE INVENTION

Advantageously a new route to prepare 2-alkoxy-derivatives of estrone and estradiol has now been found. In addition this process can also be used for the preparation of other derivatives of estradiol and estrone.

In the newly found route, aromatisation of the A-ring is carried out in the last step of the synthesis. As a result, a final product is prepared essentially free from estrogenic intermediates. Advantageously the newly found route can start from sitolactone or a derivative thereof. Sitolactone is relatively inexpensive making such a route economically more attractive than for example the route described by J. Fishman.

Accordingly this invention provides a process for the preparation of 2-substituted-derivatives of estrone and estradiol comprising i) the preparation of a compound of general formula (II) by reacting a compound of general formula (I)

(I)

in one or more steps to a compound of general formula II (II)

wherein R1 is a C2-C10 alkyl, alkenyl or aryl group; —Cl, —Br, —I, —F; —CN; —OH; or a —OR2, —O(CO)R2 or —R2—OH group, wherein R2 is an alkyl or alkylene group having 1-6 C atoms; and the bonding between atoms 9 and 10 is a single or a double bond.

ii) aromatization of the compound of general formula II to a compound of general formula III (III)

wherein R1 and R2 have the above defined meanings; and
iii) optionally, reduction of the compound of general formula III to a compound of general formula IV (IV)

wherein R1 and R2 have the above defined meanings.

Furthermore this invention provides several novel compounds, which can be intermediates in the above process, and processes to prepare these novel compounds.

Furthermore, as explained above, the process of the invention can be used to prepare 2-alkoxy-estrone or 2-alkoxy-estradiol, or mixtures thereof, containing essentially no estrogenic intermediates.

DETAILED DESCRIPTION OF THE INVENTION

As indicated above this invention provides a process for the preparation of estrone, estrone-derivates, estradiol and/or estradiol-derivates. The process is, however, especially advantageous for the preparation of 2-alkoxy derivatives of estrone and/or estradiol. In a specific embodiment, therefore, the present invention provides a process as described above for the preparation of 2-alkoxy derivatives of estrone and/or estradiol, i.e. estrone and/or estradiol substituted at position 2 with an alkoxy group. Moreover, the present invention provides such a process for the preparation of 2-methoxy-estrone and/or 2-methoxy-estradiol. As explained above such a process is especially advantageous because of the minimization of any estrogenic intermediates in the final product.

R1 in formulae II, III and IV can be a branched or straight alkyl group having from 1 to 10 carbon atoms, such as for example methyl, ethyl, propyl, isopropyl, butyl, isobutyl, tert.-butyl, pentyl, isopentyl, tert-pentyl or neo-pentyl, hexyl, heptyl, octyl, nonyl or decyl. In a specific embodiment where R1 is an alkyl group, R1 is a methyl or ethyl group. Examples of groups where R1 is an alkenyl group include ethenyl, propenyl, iso-propenyl, butenyl and pentenyl. Examples of groups where R1 is an aryl group include phenyl, benzyl and tolyl.

In a specific embodiment of the invention R1 in formula II, III and IV is —OH; or an —OR2 group, wherein R2 is an alkyl group having 1 to 6 carbon atoms. In a further embodiment R1 is an C1-C6-alkoxy group, i.e. an —OR2 group, wherein R2 is a straight or branched alkyl group having 1 to 6 carbon atoms. Examples of such alkoxy groups include methoxy-, ethoxy-, propoxy-, isopropoxy-, butyloxy-, pentyloxy, hexyloxy-. In an even further embodiment R1 in formulae II, III and IV is a methoxy or ethoxy group, and in a still further embodiment R1 is a methoxy group.

When R1 is an alkoxy group, the invention provides a process for the preparation of 2-alkoxy estrone and/or 2-alkoxy-estradiol. By reducing 2-alkoxy-estrone, prepared according to step ii) of the process, 2-alkoxy-estradiol can be obtained.

The bonding between atoms 9 and 10 in formula II can be a single or a double bond. In a specific embodiment of this invention, however, the bonding between atoms 9 and 10 is a double bond.

The aromatization in step ii) of the compound of general formula II to the compound of general formula III, can be carried out in any manner known to the skilled person to be suitable for the process. Examples of such aromatization methods include the use of an aromatization agent such as potassium tert-pentoxide, and acetic anhydride; and the use of enzymes such as aromatase.

In a specific embodiment the aromatization is carried out by potassium pentoxide.

In another specific embodiment the aromatization is carried out by using lithium in ethylene diamine.

When the bonding between atoms 9 and 10 in formula II is a double bond, the aromatization can result in two isomers of the compound of general formula III, a 9-alfa-H— and a 9-beta-H-isomer. Of these, preparation of the naturally in the human body existing 9-alfa-H isomer is preferred. Advantageously aromatization of a compound of general formula II, wherein the bonding between atoms 9 and 10 is a double bond, with lithium in ethylene diamine results in a mixture of isomers comprising a majority of the 9-alfa-H isomer.

In a further embodiment the reaction is carried out in a suitable solvent. Examples of suitable solvents include diethyl amine, tetrahydrofuran; and mixtures thereof. The temperature during the reaction can vary widely. In one embodiment the reaction is carried out at a temperature in the range from 0° to 60° C. In a specific embodiment the reaction is carried out at room temperature (20-25° C.).

In a still further embodiment the mixture is subsequently quenched with a basic solution to remove residual starting material from the mixture via an acid-base extraction.

The reduction in step iii) of the compound of general formula III to the compound of general formula IV, can be carried out in any manner known by the skilled person to be suitable for this purpose. In one embodiment the reduction is carried out with the help of a reduction agent. Examples of suitable reduction agents include $NaBH_4$ and $LiAlH_4$. In a specific embodiment $NaBH_4$ is used as a reduction agent. In a further embodiment the reaction is carried out in a suitable solvent. Examples of suitable solvents include alkanols such as methanol and ethanol; diethyl amine; tetrahydrofuran; and mixtures thereof. The temperature during the reaction can vary widely. In one embodiment the reaction is carried out at a temperature in the range from 0° to 70° C. In a specific embodiment the reaction is carried out at room temperature (20-25° C.)

Some of the compounds of general formula II are considered to be novel. Hence, this invention also provides a compound of general formula II

(II)

wherein R1 and R2 are as specified herein above; and the bonding between atoms 9 and 10 is a single or a double bond.

In a specific embodiment R1 is a C1-C6-alkoxy group, i.e. an —OR2 group, wherein R2 is a straight or branched alkyl group having 1 to 6 carbon atoms. Examples of such alkoxy groups include methoxy-, ethoxy-, propoxy-, isopropoxy-, butyloxy-, pentyloxy, hexyloxy-. In an even further embodiment R1 in formulae II, III and IV is a methoxy or ethoxy group, and in a further embodiment R1 is a methoxy group.

Advantageously the compound of general formula II is prepared from a compound with formula I, also called sito-lactone((4aS-(4aα,6aα,9aβ,9bα))-decahydro-6a-methylcyclo-penta(f)(1)benzopyran-3,7-dione).

In a specific embodiment a compound with general formula II is prepared by a process comprising the steps of
a) reacting a compound of formula I (I)

with a compound of general formula V (V)

wherein R1 and R2 have the above defined meanings; R3 and R4 independently are an alkyl group comprising 1 to 6 carbon atoms; and X is chosen from Cl or Br;

to prepare a compound of general formula (VI)

(VI)

wherein R1, R2, R3 and R4, have the above defined meanings;

b) oxidizing the hydroxy group of the compound of general formula (VI) to generate a compound of general formula (VII)

(VII)

wherein R1, R2, R3 and R4, have the above defined meanings;

c) ring-closing of the B-ring of the compound of general formula VII to prepare a compound with general formula VIII (VIII)

wherein R1, R2, R3 and R4, have the above defined meanings;

d) reacting the compound of formula VIII in one or more steps to a compound of general formula II.

In a specific embodiment the coupling reaction in step a) is carried out with help of a Grignard reaction, wherein the compound of general formula V is first converted into a compound of general formula Va.

(Va)

Suitable solvents for this reaction include diethyl ether, tetrahydrofuran and mixtures thereof.

In a specific embodiment powdered magnesium is used, which is activated with dibromoethane, whereafter the compound of general formula V is added to prepare the compound of general formula Va. The latter is added portion wise into a solution or suspension comprising the compound of general formula I to generate a compound of general formula VI. In a further embodiment the reaction is carried out at refluxing temperature and at atmospheric pressure (1 bar). Preferably the obtained product is purified by crystallisation from a 1:1 mixture of heptane and ethyl acetate.

The oxidation of the hydroxy group of the compound of general formula VI to generate a compound of general formula VII in step b) can be carried out by any oxidation method known by the skilled person to be suitable for this purpose. Examples of suitable oxidation methods include the treatment with an oxidation agent such as chromic acid, chromium oxide/pyridine, chlorine/pyridine, calcium dichromate, pyridine chromates and N-bromosuccinimide; and the Oppenauer oxidation. In one specific embodiment the oxidation is carried out by oxidation with chromic acid in acetone. In a second embodiment the oxidation is carried out with tetra-n-propyl ammonium perruthenate (TPAP) and N-methylmorpholine N-oxide (NMO). As an alternative solvent dichloromethane can be used.

The ring-closing of the B-ring of the compound of general formula VII to prepare a compound with general formula VIII in step c) can be carried out in any manner known by the skilled person to be suitable for this purpose. By the B-ring is understood those carbon atoms that form the B-ring in the final product estrone- or estradiol derivate. In one specific embodiment the ring-closing step is carried out by an aldol condensation under alkaline conditions, which condensation is in a further embodiment followed by a dehydration of the aldol product. Examples of suitable bases that can be used include potassium-tert-butoxide, potassium-tert-pentoxide, sodium hydroxide, potassium hydroxide. The skilled person will further recognize that many more bases can be used. In a further embodiment the reaction is carried out in a suitable solvent. Examples of suitable solvents include toluene; alkanols such as methanol, ethanol and isopropanol; tetrahydrofuran; and mixtures thereof. In a specific embodiment a mixture of methanol, toluene and water is used as a solvent. The temperature during the reaction can vary widely. In one embodiment the reaction is carried out at a temperature in the range from 0° to 80° C. In a specific embodiment the reaction is carried out at room temperature (20°-25° C.). In another specific embodiment the reaction is carried out at a temperature in the range from 55° to 75° C. In a further embodiment the obtained compound of general formula VIII is purified by crystallisation from a suitable solvent such as an alcohol. In a specific embodiment the compound of general formula VIII is purified by crystallisation in isopropanol.

The preparation of a compound of general formula II from the compound of general formula VIII according to step d) can be carried out by any manner known by the skilled person to be suitable for this purpose. In one specific embodiment the reaction of step d) comprises d1) hydrolysis of a compound of general formula VIII, wherein the bonding between atoms 9 and 10 is a double bond, to obtain a compound of general formula IX,

(IX)

wherein R1 and R2 have the above defined meanings;

d2) ring-closure of the A-ring to obtain a compound of general formula II, wherein the dotted bonding between atoms 9 and 10 is a double bond, from the compound of general formula IX.

In an alternative embodiment the reaction of step d) comprises d3) hydrogenation of the double bond between atoms 9 and 10 of the compound of general formula VIII to obtain a compound of general formula X;

(X)

d4) hydrolysis of the compound of general formula X to obtain a compound of general formula XI;

(XI)

d5) ring-closure of the A-ring in the compound of general formula XI, to obtain a compound of general formula II, wherein the dotted bonding between atoms 9 and 10 is a single bond.

By the A-ring is understood those carbon atoms that form the A-ring in the final product estrone- or estradiol derivate.

The hydrolysis of step d1) can be carried out in any manner known by the skilled person to be suitable for this purpose. In one embodiment the hydrolysis is carried out under acidic conditions. Examples of suitable hydrolysis agents include hydrohalogens, phosphoric acids, sulfonic and sulfuric acids, such as hydrochloric acid, sulfuric acid, para-toluene sulfonic acid and phosphoric acid. In one embodiment sulfuric acid ($H_2SO_4$) is used as a hydrolysis agent. Any solvent known by the skilled person to be suitable for this purpose can be used as solvent during the reaction. Examples of suitable solvents include C1-C6 alkanols, such as methanol, ethanol, propanol and isopropanol. In one embodiment ethanol is used as a solvent. The temperature during the reaction can vary widely. In one embodiment the reaction is carried out at a temperature in the range from 0° to 40° C., and in a specific embodiment the reaction is carried out at room temperature (20°-25° C.).

The ring-closure of the A-ring of step d2) can be carried out in any manner known by the skilled person to be suitable for this purpose. In one specific embodiment the ring-closing step is carried out by an aldol condensation under alkaline conditions, which condensation is in a further embodiment followed by a dehydration of the aldol product. Examples of suitable bases that can be used include potassium-tert-butoxide, potassium-tert-pentoxide, sodium hydroxide, potassium hydroxide. The skilled person will further recognize that many more bases can be used. In a further embodiment the reaction is carried out in a suitable solvent. Examples of suitable solvents include toluene; alkanols such as methanol, ethanol and isopropanol; tetrahydrofuran; and mixtures thereof. The temperature during the reaction can vary widely. In one embodiment the reaction is carried out at a temperature in the range from 0° to 80° C. In a specific embodiment the reaction is carried out at room temperature (20°-25° C.)

The hydrogenation of step d3) can be carried out in any manner known by the skilled person to be suitable for this purpose. In one embodiment Pd/C and hydrogen are used for the hydrogenation. In a further embodiment the reaction is carried out in a suitable solvent. Examples of suitable solvents include tetrahydrofuran; alkanols such as methanol, ethanol and isopropanol; and mixtures thereof. In a specific embodiment ethanol is used as a solvent. The temperature during the reaction can vary widely. In one embodiment the reaction is carried out at a temperature in the range from 0° to 80° C. In a specific embodiment the reaction is carried out at a temperature in the range from 25° to 60° C.

The hydrolysis of step d4) can be carried out in any manner known by the skilled person to be suitable for this purpose. In one embodiment the hydrolysis is carried out under acidic conditions. Examples of suitable hydrolysis agents include hydrohalogens, phosphoric acids, sulfonic and sulfuric acids, such as hydrochloric acid, sulfuric acid, para-toluene sulfonic acid and phosphoric acid. In one embodiment sulfuric acid ($H_2SO_4$) is used as a hydrolysis agent. Any solvent known by the skilled person to be suitable for this purpose can be used as solvent during the reaction. Examples of suitable solvents include C1-C6 alkanols, such as methanol, ethanol, propanol and isopropanol. In one embodiment ethanol is used as a solvent. The temperature during the reaction can vary widely. In one embodiment the reaction is carried out at a temperature in the range from 0° to 40° C., and in a specific embodiment the reaction is carried out at room temperature (20°-25° C.).

The ring-closure of the A-ring of step d5) can be carried out in any manner known by the skilled person to be suitable for this purpose. In one specific embodiment the ring-closing step is carried out by an aldol condensation under alkaline conditions, which condensation is in a further embodiment followed by a dehydration of the aldol product. Examples of suitable bases that can be used include potassium-tert-butoxide, potassium-tert-pentoxide, sodium hydroxide, potassium hydroxide. The skilled person will further recognize that many more bases can be used. In a further embodiment the reaction is carried out in a suitable solvent. Examples of suitable solvents include toluene; alkanols such as methanol, ethanol and isopropanol; tetrahydrofuran; and mixtures thereof. The temperature during the reaction can vary widely. In one embodiment the reaction is carried out at a temperature in the range from 0° to 80° C. In a specific embodiment the reaction is carried out at room temperature (20°-25° C.)

A number of the above mentioned intermediates are considered novel. Hence the present invention also provides a compound of general formula V (V)

and its Mg activated counterpart of general formula Va (Va)

wherein R1, R2, R3 and R4, have the above defined meanings; and X is chosen from Cl or Br. In a further embodiment R3 and R4 are independently methyl or ethyl groups. In a specific embodiment R3 and R4 are methyl groups and R1 is a methoxy group. Examples of suitable compounds according to general formula V include for example 2-(3-chloro-1-methoxy-propyl)-2,5,5-trimethyl-[1,3]dioxane and 2-(3-bromo-1-methoxy-propyl)-2,5,5-trimethyl-[1,3]dioxane. Examples of suitable compounds according to general formula Va include for example 3-methoxy-2-pentanone-neopentylacetale-5-magnesium chloride and 3-methoxy-2-pentanone-neopentylacetale-5-magnesium bromide.

Figure 1:
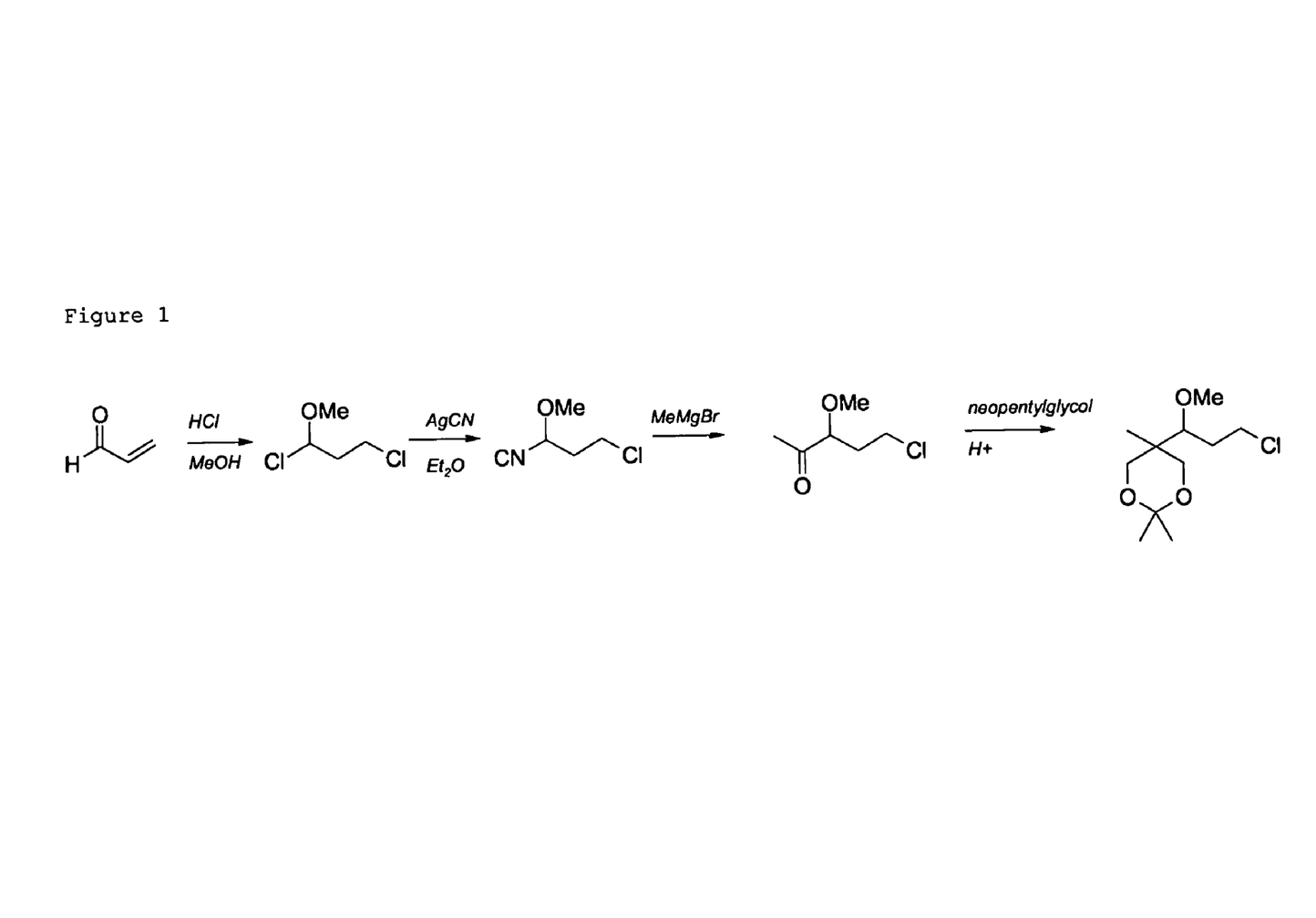
FIG. 1: Reaction scheme for the preparation of 2-(3-chloro-1-methoxy-propyl)-2,5,5,-trimethyl-[1,3]dioxane.

The compounds of general formula (V) can for example be prepared by halogenation of a suitably substituted propene compound; substitution of one halogen atom by a nitrile group; addition of a methyl group by a grignard reaction and conversion into the 5-chloro-pentan-2-one compound substituted at its 3 position by an appropriate group; and reaction with neopentylglycol under acidic conditions to obtain the compound of general formula (V). The preparation of 2-(3-chloro-1-methoxy-propyl)-2,5,5-trimethyl-[1,3]dioxane is illustrated in FIG. 1.

Furthermore the invention provides a compound of general formula (VI)

(VI)

wherein R1, R2, R3 and R4, have the above defined meanings.

Even further the invention provides a compound of general formula VII (VII)

wherein R1, R2, R3 and R4, have the above defined meanings.

Even further the invention provides a compound with general formula VIII (VIII)

wherein R1, R2, R3 and R4, have the above defined meanings.

Even further the invention provides a compound of general formula IX, (IX)

wherein R1 and R2 have the above defined meanings.

Even further the invention provides a compound of general formula X, (X)

wherein R1, R2, R3 and R4 are as defined above.

Even further the invention provides a compound of general formula XI (XI)

wherein R1 and R2 are as defined above.

Figure 2:
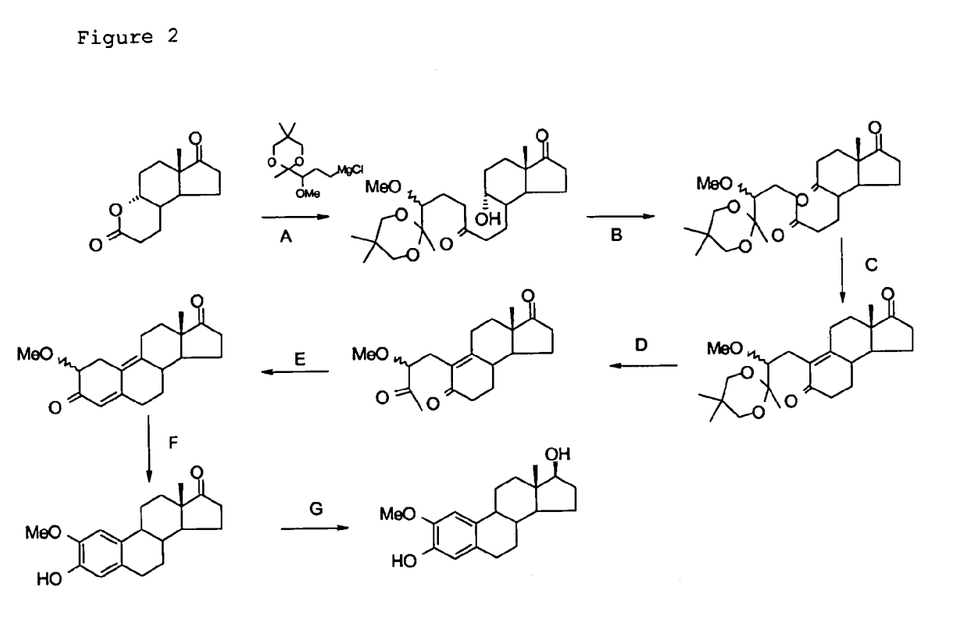
FIG. 2: Reaction scheme for the preparation of 2-methoxyestradiol.

The invention is illustrated by the following non-limiting examples and the reaction scheme in FIG. 2.

EXAMPLE 1

Step A: Preparation of (3aα,4α,5α,7aα)5-hydroxy-7a-methyl-4[7-(2,5,5-trimethyl-1,3-dioxan-2-yl)-5-methoxy-3-oxohexyl]-1H-inden-1-one Magnesium powder 50 Mesh (10 g) was suspended in dry tetrahydrofuran (70 ml). The suspension was heated up to 50° C. After adding dibromoethane (500 μl), a vigorous reaction occurred. An initial portion of 2-(3-chloro-1-methoxy-propyl)-2,5,5-trimethyl-[1,3]dioxane (2 g) was added.

After 1 h stirring at reflux 2-(3-chloro-1-methoxy-propyl)-2,5,5-trimethyl-[1,3]dioxane (35 g) was added.

After stirring at reflux for 20 h the reaction mixture was cooled to 20° C.

The unreacted magnesium was allowed to settle down and the upper layer was taken up in a syringe and added to a suspension of (4aS-(4aα,6aα,9aα,9bα))-decahydro-6a-methylcyclo-penta(f)(1)benzopyran-3,7-dione (sitolactone, 28 g) in tetrahydrofuran (110 ml) at −35° C.

After stirring for 4 h at −30° C. the temperature was increased to 20° C. in 1 h.

A solution of ammonium chloride (10 g in 200 ml water) was added drop wise to the reaction mixture in 40 min.

The suspension was stirred for 1 h and filtered over a Dicalite® filter.

The filter was washed with dichloromethane (2×100 ml).

After a solvent free distillation in vacuo at 30° C., the residue was extracted with dichloromethane (5×100 ml).

The organic layers were combined and concentrated in vacuo at 30° C.

After drying 51.6 g crude (3aα,4α,5α,7aα)5-hydroxy-7a-methyl-4[7-(2,5,5-trimethyl-1,3-dioxan-2-yl)-5-methoxy-3-oxohexyl]-1H-inden-1-one was obtained.

EXAMPLE 2

Step B: Preparation of (3aα,4β,5α,7aβ)-5-oxo-7a-methyl-4[6-(2,5,5-trimethyl-1,3-dioxan-2-yl)-5-methoxy-3-oxohexyl]-1H-inden-1-one, oxidation of the hydroxy group To a solution of (3aα,4α,5α,7aα)5-hydroxy-7a-methyl-4[7-(2,5,5-trimethyl-1,3-dioxan-2-yl)-5-methoxy-3-oxohexyl]-1H-inden-1-one (85 g) in dichloromethane (450 ml), N-methylmorpholine (35 g) and tetrapropyl ammoniumperruthenate (2 g) were added at 20° C.

After stirring at 20° C. for 20 h silica (50 g) was added.

The reaction mixture was filtered over a Dicalite® filter with silica and the filter was washed with dichloromethane (500 ml).

The filtrate was evaporated to dryness at 30° C.

75.36 g crude (3aα,4β,5α,7aβ)-5-oxo-7a-methyl-4[6-(2,5,5-trimethyl-1,3-dioxan-2-yl)-5-methoxy-3-oxohexyl]-1H-inden-1-one was obtained containing about 10% starting material.

EXAMPLE 3

Step C: Preparation of (3aα,9aα,9bβ)-4,5,8,9,9a,9b-hexahydro-3a-methyl-6-(2-(2,5,5-trimethyl-1,3-dioxan-2-yl)-1-methoxy-ethyl)-1H-benz(e)indene-3,7(2H,3aH)-dione, formation of the B-ring Potassium tert-butoxide (6.4 g) was suspended in toluene (100 ml) and 2-propanol (32 ml) at 20° C.

A solution of (3aα,4α,5α-7aα)-5-oxo-7a-methyl-4[6-(2,5,5-trimethyl-1,3-dioxan-2-yl)-5-methoxy-3-oxohexyl]-1H-inden-1-one (80 g) in toluene (400 ml) was added to the Potassium tert-butoxide/toluene/2-propanol mixture in 30 min.

After stirring the reaction mixture for 2 h at 20° C., the reaction mixture was acidified with acetic acid (8 ml) to pH=4.

After adding water (300 ml) and stirring for 15 min at 20° C., the layers were separated.

The water layer was extracted with toluene (3×100 ml) and the combined organic layer was extracted with a solution of sodium hydroxide (5 g) in water (100 ml). The organic layer was evaporated to dryness in vacuo at 50° C.

The residue was dissolved in 2-propanol (300 ml) at 50° C. and the solution was cooled to 10° C.

After stirring for 2 h at 10° C. a first crop of white crystals (7.8 g) was obtained.

The mother liquor was evaporated to dryness and taken up in heptane (50 ml).

The solution was stirred at 70° C. for 30 min and then cooled to 20° C.

After stirring the suspension at 20° C. for 50 h, a second crop of white crystals (11.5 g) was obtained.

EXAMPLE 4

Step B and C: Preparation of (3aα,9aα,9bβ)-4,5,8,9,9a,9b-hexahydro-3a-methyl-6-(2-(2,5,5-trimethyl-1,3-dioxan-2-yl)-1-methoxy-ethyl)-1H-benz(e)indene-3,7(2H,3aH)-dione; Combined oxidation and aldol condensation A solution of (3aα,4α,5α,7aα)5-hydroxy-7a-methyl-4[7-(2,5,5-trimethyl-1,3-dioxan-2-yl)-5-methoxy-3-oxohexyl]-1H-inden-1-one (147 g) in a mixture of toluene (690 ml) and pyridine (162 ml) was cooled to −2° C.

Chlorine gas (42 g) was led into the reaction mixture in 2 h. After stirring the reaction mixture at −2° C. for 2 h, the reaction mixture was poured into a solution of sodium sulfite (93 g) and sodium carbonate (78 g) in water (750 ml) at 10° C. The mixture was stirred at 20° C. for 30 min and the layers were separated. The water layer was extracted with toluene (4×150 ml).

The combined organic layer was evaporated to dryness in vacuo at 50° C.

The residue was dissolved in toluene (660 ml).

A solution of potassium hydroxide (127.5 g) in water (185 ml) and methanol (430 ml) was added to the toluene solution.

After stirring at 65° C. for 45 min the reaction mixture was cooled to 20° C.

The layers were separated and the organic layer was washed with 50% methanol (aq) (2×175 ml). The combined methanol/water extracts were washed with dichloromethane (4×100 ml). The combined organic layer was evaporated to dryness in vacuo at 40° C. and the residue was suspended in 2-propanol (250 ml) at 50° C.

After stirring at 50° C. for 15 min the suspension was stirred for 1 h at 10° C. and the crystals were filtered off and washed with 2-propanol (2×10 ml).

After drying 58.04 g product was obtained.

EXAMPLE 5

Step D: Preparation of 2-methoxy-(+)-4,5-seco-estr-9-en-3,5,17-trione, hydrolysis of the ketal To a suspension of (3aα,9aα,9bα)-4,5,8,9,9a,9b-hexahydro-3a-methyl-6-(2,5,5-trimethyl-1,3-dioxan-2-yl)-1-methoxy-ethyl)-1H-benz(e)indene-3,7(2H,3aH)-dione (16.2 g) in ethanol (200 ml) sulfuric acid (2 ml) was added to the suspension (pH=2) at 20° C.

The reaction mixture was stirred at 40° C. for 2 h.

A solution of sodium acetate (3.5 g) in water (100 ml) was added to the reaction mixture.

The reaction mixture was cooled to 20° C.

After adding dichloromethane (100 ml) and water (100 ml) the mixture was stirred for 30 min at 20° C. and the layers were separated.

The water layer was extracted with dichloromethane (3×50 ml). The dichloromethane extracts were combined and evaporated to dryness at 50° C., obtaining 16.7 g crude product.

EXAMPLE 6

Step E: Preparation and purification of 2-methoxy-estra-4,9-diene-3,17-dione, formation of the A-ring A solution of 2-methoxy-(+)4,5-seco-estr-9-en-3,5,17-trione (10 g) in tetrahydrofuran (50 ml) was added in 30 min to a suspension of Potassium tert-butoxide (750 mg) in tetrahydrofuran (50 ml) at 20° C.

After stirring at 20° C. for 7 h the reaction mixture was neutralized to pH=6 with 4.0 N sulfuric acid.

The reaction mixture was concentrated in vacuo at 35° C.

The residue was dissolved in dichloromethane (100 ml) and extracted with water (2×50 ml).

The organic layer was evaporated to dryness at 35° C. and 8.1 g crude product was obtained.

EXAMPLE 7

Step F: Preparation of 2-methoxy-estrone, aromatisation

Lithium (0.58 g) was slowly added to ethylene diamine (100 ml) at 100° C.

After stirring the mixture for 30 min at 100° C. it was cooled to 20° C.

A solution of 2-methoxy-estra-4,9-diene-3,17-dione (5 g) in ethylene diamine (20 ml) was added in 30 min to the reagent at 20° C.

After stirring for 3 h at 20° C. the reaction mixture was poured into water (250 ml).

It was acidified with sulfuric acid to pH=7.

After stirring for 12 h at 20° C. light brown crystals were obtained and filtered off.

The crude product (6 g) was filtered over silica to remove the inorganic salts, yielding 1.7 g product. The ratio of formed 9α-H isomer to formed 9α-H isomer was about 7:1.

EXAMPLE 8

Step F: Preparation of 2-methoxy-estrone, aromatisation

At 20° C. 2-methoxy-estra-4,9-diene-3,17-dione (500 mg, 1.66 mmol) was dissolved in tetrahydrofuran (12.5 ml). Hereafter a solution of 1.7 M potassium tert-pentoxide in toluene (5 ml toluene, 8.5 mmol potassium tert-pentoxide) was added. The reaction was quenched with 25 ml of a 1 M Sodium hydroxide (NaOH) solution. The aqueous layer was separated and the pH was brought to 4 with 2M sulfuric acid. After extraction with three portions of dichloromethane (15 ml), 200 mg crude product was obtained via evaporation to dryness of the organic layer.

The first organic layer (tetrahydrofuran/toluene) appeared to contain a considerable amount of product. After evaporation to dryness 250 mg product was obtained.

The ratio of formed 9α-H isomer to formed 9α-H isomer was about 1:1.

EXAMPLE 9

Step G: Preparation of 2-methoxy-estradiol, reduction

To a solution of 2-methoxyestrone (2 g) in tetrahydrofuran (15 ml) 33% sodium hydroxide (200 µl) and water (2 ml) were added at 20° C.

Sodium borohydride (0.25 g) was slowly added to the reaction mixture.

The reaction mixture was stirred for 1 h at 20° C. and neutralized with acetic acid to pH=7.

After stirring for 30 min the layers were separated and the water layer was extracted with dichloromethane (2×10 ml). The organic layers were combined and evaporated to dryness at 35° C.

The residue (2.1 g) was chromatographed over silica (200 g) with a mixture of toluene and ethyl acetate (volume-ratio of toluene to ethyl acetate 9:1).

Crystallizations from acetone and ethanol yielded 400 mg 2-methoxyestradiol.

The invention claimed is:

1. A process for the preparation of 2-substituted-derivatives of estrone and estradiol comprising
    i) the preparation of a compound of formula (II) by reacting a compound of formula (I)

in one or more steps to a compound of formula II wherein R1 is a C1-C10 alkyl, alkenyl or aryl group; —Cl, —Br, —I, —F; —CN; —OH; or a —OR2, —O(CO)R2 or —R2—OH group, wherein R2 is an alkyl or alkylene group having 1-6 C atoms; and the bonding between atoms 9 and 10 is a single or a double bond ii) aromatization of the compound of formula II to a compound of formula III wherein R1 and R2 have the above defined meanings; and
iii) optionally, reduction of the compound of formula III to a compound of formula IV wherein R1 and R2 have the above defined meanings.

2. The process according to claim 1, wherein in the compounds of formulae II, Ill, and IV R1 is an —OR2 group, wherein R2 is an alkyl group having 1 to 6 carbon atoms.

3. The process according to claim 1, wherein in the compound of formula II the bonding between atoms 9 and 10 is a double bond.

4. The process according to claim 1, wherein the aromatization in step ii) is carried with the help of lithium in ethylene diamine.

5. The process according to claim 1, wherein the reduction in step iii) is carried out using $NaBH_4$ as a reduction agent.

* * * * *